US012685693B2

(12) United States Patent
Nelson et al.

(10) Patent No.: US 12,685,693 B2
(45) Date of Patent: Jul. 21, 2026

(54) DRUG WASTE DEPOSITORY SYSTEMS, APPARATUSES, AND METHODS

(71) Applicant: Vigilant Waste Technologies, Inc., Austin, TX (US)

(72) Inventors: David A. Nelson, Austin, TX (US); Alfred R. Baddour, Austin, TX (US)

(73) Assignee: Vigilant Waste Technologies, Inc., Austin, TX (US)

( * ) Notice: Subject to any disclaimer, the term of this patent is extended or adjusted under 35 U.S.C. 154(b) by 355 days.

(21) Appl. No.: 18/226,634

(22) Filed: Jul. 26, 2023

(65) Prior Publication Data

US 2024/0033178 A1 Feb. 1, 2024

Related U.S. Application Data

(60) Provisional application No. 63/392,672, filed on Jul. 27, 2022.

(51) Int. Cl.
A61J 1/05 (2006.01)
A61J 1/18 (2023.01)
(Continued)

(52) U.S. Cl.
CPC . A61J 1/05 (2013.01); A61J 1/18 (2013.01); G16H 10/60 (2018.01); G16H 20/10 (2018.01); G16H 40/63 (2018.01)

(58) Field of Classification Search
CPC ... A61J 1/05; A61J 1/18; G16H 10/60; G16H 20/10; G16H 40/63; G16H 40/20; G16H 70/40; A61B 50/30
See application file for complete search history.

(56) References Cited

U.S. PATENT DOCUMENTS

| | | | |
|---|---|---|---|
| 4,900,500 A | 2/1990 | Honeycutt | |
| 5,038,929 A | 8/1991 | Kubofcik | |

(Continued)

FOREIGN PATENT DOCUMENTS

| | | |
|---|---|---|
| CN | 210479739 | 5/2020 |
| CN | 217987920 | 12/2022 |
| WO | 01/08824 | 2/2001 |

OTHER PUBLICATIONS

International Searching Authority, International Search Report and Written Opinion for International Patent Application No. PCT/US2024/039107 dated Sep. 17, 2024, 10 pages.

*Primary Examiner* — Ryan W Sherwin

(74) *Attorney, Agent, or Firm* — Egan, Enders & Huston LLP.

(57) ABSTRACT

Apparatuses and systems are provided which include a drug waste depository apparatus with a housing having a waste input port and a chamber, wherein the chamber comprises a waste inlet coupled to the waste input port and a waste outlet. The housing includes an interior space for receiving a removable module that is configured to analyze, sequester, and/or adulterate one or more drugs. The system is configured such that the waste outlet of the chamber may be coupled to an inlet of a received module and is further configured such that the waste outlet of the chamber may be closed when the interior space is void of a module. In addition, a drug waste depository apparatus is provided which is programmed to selectively route a drug from a first chamber to a second chamber of the apparatus based on information received at an electronic user interface of the apparatus.

19 Claims, 2 Drawing Sheets

(51) Int. Cl.
  G16H 10/60        (2018.01)
  G16H 20/10        (2018.01)
  G16H 40/63        (2018.01)

(56)                References Cited

U.S. PATENT DOCUMENTS

| | | | |
|---|---|---|---|
| 5,213,884 | A | 5/1993 | Fellows |
| 5,284,772 | A | 2/1994 | Oxley |
| 6,010,444 | A | 1/2000 | Honeycutt et al. |
| 6,203,484 | B1 | 3/2001 | Lepore et al. |
| 6,592,768 | B1 | 7/2003 | Lepore et al. |
| 6,868,344 | B1 | 3/2005 | Nelson |
| 7,120,487 | B2 | 10/2006 | Nelson |
| 7,184,897 | B2 | 2/2007 | Nelson |
| 7,458,741 | B2 | 12/2008 | Detwiler et al. |
| 7,673,825 | B2 | 3/2010 | Jeansonne et al. |
| 7,892,420 | B2 | 2/2011 | Dunn et al. |
| 8,195,328 | B2 | 6/2012 | Mallett et al. |
| 8,348,056 | B2 | 1/2013 | Maness |
| 8,490,795 | B2 | 7/2013 | Ziemba |
| 8,534,459 | B2 | 9/2013 | Maness |
| 8,573,426 | B2 | 11/2013 | Maness |
| 8,606,596 | B1 | 12/2013 | Bochenko et al. |
| 8,616,397 | B2 | 12/2013 | Maness |
| 8,684,968 | B2 | 4/2014 | Genosar |
| 8,740,866 | B2 | 6/2014 | Reasoner et al. |
| 9,302,134 | B1 | 4/2016 | Nelson et al. |
| 9,456,958 | B2 | 10/2016 | Reddy et al. |
| 9,796,526 | B2 | 10/2017 | Smith et al. |
| 10,032,344 | B2 | 7/2018 | Nelson et al. |
| 10,155,127 | B1 | 12/2018 | Nelson et al. |
| 10,249,153 | B2 | 4/2019 | Nelson et al. |
| 11,097,141 | B2 | 8/2021 | Nelson et al. |
| 2008/0058736 | A1 | 3/2008 | Reshamwala |
| 2008/0190953 | A1 | 8/2008 | Mallett et al. |
| 2008/0217447 | A1 | 9/2008 | Jeansonne et al. |
| 2009/0294312 | A1* | 12/2009 | Hitson ............... B65F 1/10 206/364 |
| 2010/0241270 | A1* | 9/2010 | Eliuk ............... A61J 1/20 700/216 |
| 2011/0064624 | A1 | 3/2011 | McGee et al. |
| 2011/0259467 | A1* | 10/2011 | Maness ............. A61B 50/36 141/391 |
| 2012/0088951 | A1 | 4/2012 | Deryck et al. |
| 2012/0226447 | A1* | 9/2012 | Nelson ............. G16H 40/60 702/25 |
| 2012/0305132 | A1 | 12/2012 | Maness |
| 2012/0323061 | A1 | 12/2012 | Stalons |
| 2013/0018356 | A1* | 1/2013 | Prince ........... G06Q 10/0833 604/506 |
| 2013/0325727 | A1 | 12/2013 | MacDonell et al. |
| 2014/0008259 | A1 | 1/2014 | Maness |
| 2015/0152348 | A1* | 6/2015 | Tusa ............... C10L 5/48 44/605 |
| 2015/0315045 | A1 | 11/2015 | Sanborn et al. |
| 2017/0029209 | A1 | 2/2017 | Smith et al. |
| 2017/0203138 | A1* | 7/2017 | Anderson ........... B01J 20/20 |
| 2019/0091504 | A1* | 3/2019 | Nelson ............... B09B 3/35 |
| 2019/0217352 | A1 | 7/2019 | Maness et al. |
| 2020/0289740 | A1* | 9/2020 | Tamtoro ........... A61J 7/0409 |
| 2023/0207091 | A1* | 6/2023 | Joyce ............... G16H 20/17 705/3 |
| 2024/0212815 | A1* | 6/2024 | Lafauci ............. G16H 20/10 |

* cited by examiner

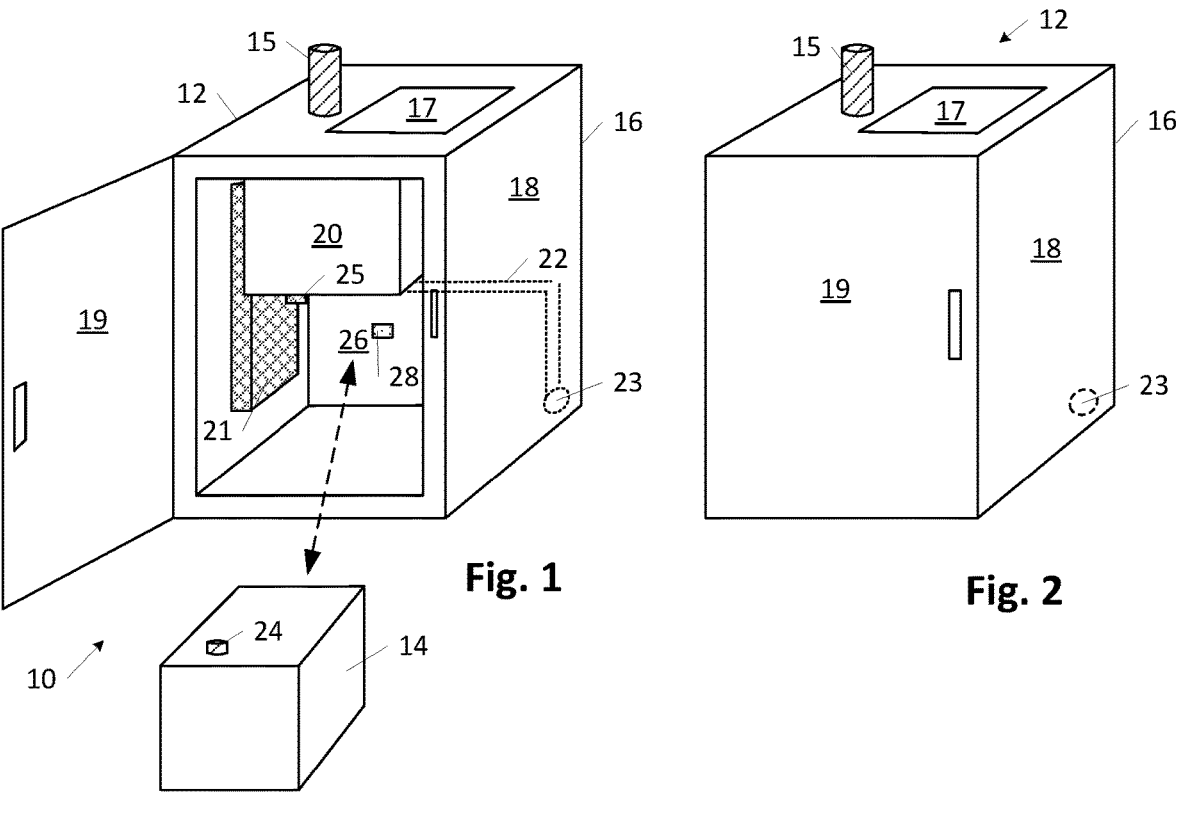

Fig. 1

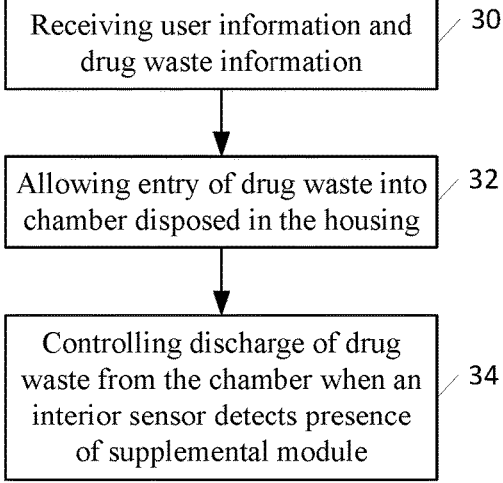

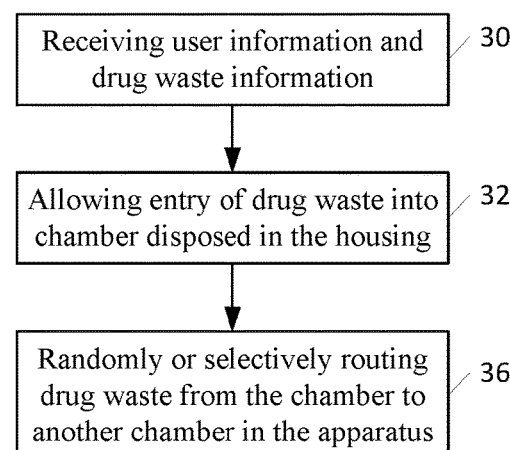

Fig. 2

| Receiving user information and drug waste information | / 30 |
| :--- | :--- |

↓

| Allowing entry of drug waste into chamber disposed in the housing | / 32 |
| :--- | :--- |

↓

| Controlling discharge of drug waste from the chamber when an interior sensor detects presence of supplemental module | / 34 |
| :--- | :--- |

Fig. 3

| Receiving user information and drug waste information | / 30 |
| :--- | :--- |

↓

| Allowing entry of drug waste into chamber disposed in the housing | / 32 |
| :--- | :--- |

↓

| Randomly or selectively routing drug waste from the chamber to another chamber in the apparatus | / 36 |
| :--- | :--- |

Fig. 4

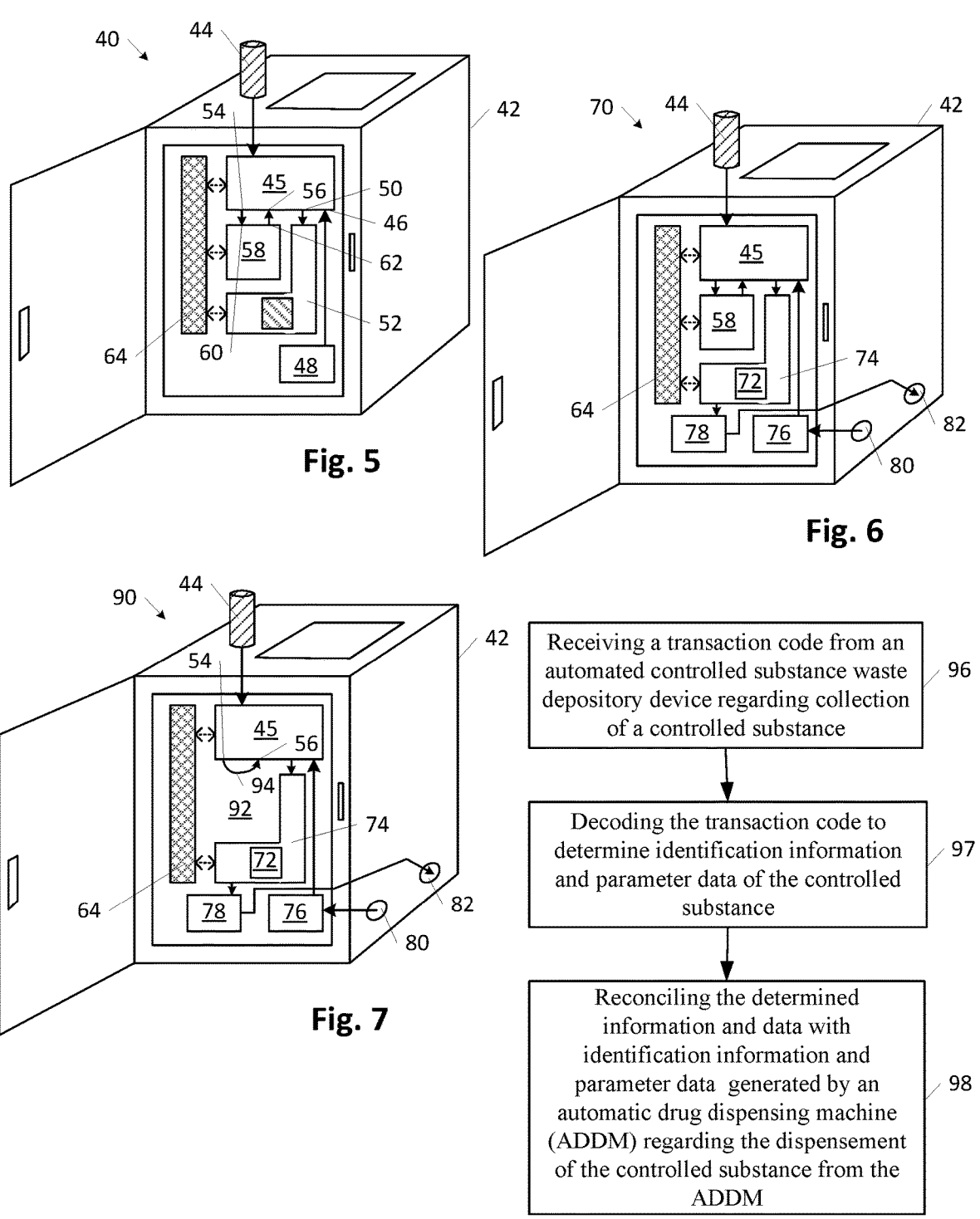

Receiving a transaction code from an automated controlled substance waste depository device regarding collection of a controlled substance　96

Decoding the transaction code to determine identification information and parameter data of the controlled substance　97

Reconciling the determined information and data with identification information and parameter data generated by an automatic drug dispensing machine (ADDM) regarding the dispensement of the controlled substance from the ADDM　98

Fig. 8

DRUG WASTE DEPOSITORY SYSTEMS, APPARATUSES, AND METHODS

PRIORITY CLAIM

The present application claims priority to U.S. Provisional Patent Application No. 63/392,672 filed Jul. 27, 2022.

BACKGROUND OF THE INVENTION

1. Field of the Invention

The invention relates generally to the disposal of drugs. Specifically, this invention relates to methods, systems, and apparatuses for the collection and disposal of excess, unwanted, tainted, recalled, or expired drugs.

2. Description of the Related Art

The following descriptions and examples are not admitted to be prior art by virtue of their inclusion within this section.

In effort to promote the secure, convenient, and responsible disposal of drugs and further to prevent and detect the diversion of controlled substances for illicit uses, drug depository devices and receptacles are provided in places at which drugs are commonly administered, such as within retail pharmacies and patient care centers (e.g., hospitals, ambulatory surgery centers and specialty procedure centers). Some of such devices and receptacles are configured to analyze waste deposited therein in order to determine or verify the identity, concentration and/or volume of the waste. In addition or alternatively, some devices and receptacles are configured to adulterate received drug waste. Such provisions aid in deterring the diversion of controlled substances for illicit purposes. However, analytical systems and adulteration systems increase the cost of a drug depository receptacle/device as well as the processing time for each waste.

It is therefore desirable to develop methods, apparatuses and systems for the collection and disposal of excess, unwanted, tainted, recalled, or expired drugs that are cheaper and/or more efficient than conventional devices, but yet provide means to deter the diversion of drugs for illicit purposes.

SUMMARY OF THE INVENTION

Methods, systems, and apparatuses are provided for the collection and disposal of excess, unwanted, tainted, recalled, or expired drugs. The following description of various embodiments of program instructions, systems, and apparatuses is not to be construed in any way as limiting the subject matter of the appended claims.

An embodiment of a drug waste depository apparatus includes a housing having opaque walls, an opaque door, and a waste input port. In addition, the drug waste depository apparatus includes a chamber disposed within the housing, wherein the chamber includes a waste inlet coupled to the waste input port. Furthermore, the drug waste depository apparatus includes an interior space within the housing separate from the chamber and accessible when the opaque door is open. Moreover, the drug waste depository apparatus includes a first sensor for detecting presence of an item in the interior space and a second sensor for detecting whether the opaque door is closed, wherein the apparatus is void of an indicator of whether an item occupies or does not occupy the interior space when the opaque door is closed.

Another embodiment of a drug waste depository apparatus includes a housing having a waste input port and a first chamber disposed in the housing, wherein the first chamber includes a waste inlet coupled to the waste input port and a waste outlet. The drug waste depository apparatus further includes a second chamber disposed within the housing having an inlet coupled to the waste outlet of the first chamber. In addition, the drug waste depository apparatus includes an electronic user interface, a processor, and a storage medium comprising program instructions executable by the processor for receiving information from the electronic user interface regarding an individual depositing a drug in the waste input port. Moreover, the storage medium includes program instructions executable by the processor for randomly routing fluid from the first chamber to the second chamber or selectively routing fluid from the first chamber to the second chamber based on the received information.

An embodiment of a system includes one or more modules each configured to sequester, analyze, and/or adulterate one or more drugs. In addition, the system includes one or more drug waste depository apparatuses each including a housing having a waste input port and a chamber disposed in the housing, wherein the chamber comprises a waste inlet coupled to the waste input port and a waste outlet. Furthermore, the one or more drug waste depository apparatuses each include an interior space in the housing configured to receive one of the one or more modules. The system is configured such that the waste outlet of the chamber may be coupled to an inlet of a received module and is further configured such that the waste outlet of the chamber may be closed when the interior space is void of a module.

An embodiment of a storage medium includes program instructions which are executable by a processor for receiving a transaction code from an automated controlled substance waste depository device regarding collection of a controlled substance and decoding the transaction code to determine identification information and parameter data of the controlled substance. Furthermore, the storage medium includes program instructions which are executable by a processor for reconciling the determined identification information and parameter data with identification information and parameter data generated by an automatic drug dispensing machine regarding the dispensement of the controlled substance from the automatic drug dispensing machine.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 is an isometric view of a system comprising a drug waste depository apparatus and a removable module;

FIG. 2 is an isometric view of the drug waste depository apparatus of FIG. 1 with its front door closed;

FIG. 3 is a flowchart of operations for a drug waste depository apparatus;

FIG. 4 is a flowchart of other operations for a drug waste depository apparatus;

FIG. 5 is a schematic view of components and flow in a drug waste depository apparatus;

FIG. 6 is a schematic view of components and flow in another drug waste depository apparatus;

FIG. 7 is a schematic view of components and flow in yet another drug waste depository apparatus; and

FIG. 8 is a flowchart of processes for reconciling information regarding a drug disposed of in an automatic controlled substance waste depository versus information regarding the dispensement of the drug from an automatic drug dispensing machine.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The disclosure herein relates generally to the collection and disposal of drugs. As set forth in more detail below, the methods, program instructions, apparatuses and systems described herein may have particular application for collection and disposal of prescription drugs. It is noted, however, that the methods, program instructions, apparatuses, and systems described herein are not restricted to applications of prescription medications. In particular, the methods, program instructions, apparatuses, and systems described herein may be used for the collection and disposal of any drug. In some cases, the apparatuses and systems described herein may be used and, in some embodiments, may be specifically configured to receive, analyze and/or process a variety of drug forms. In other cases, the apparatuses and systems described herein may be used and, in some embodiments, may be specifically configured to receive, analyze and/or process a single form of a drug. Different forms of drugs which may be considered for collection and disposal in the apparatuses and systems described herein include but are not limited to liquids, pills, powders, and patches.

The term "drug", as used herein, refers to a substance other than food that has a physiological effect when introduced into or applied onto the body. The term is inclusive to controlled substances, such as prescription medication and drugs used for nonmedicinal purposes, as well as over-the-counter drugs. As used herein, the term "controlled substance" refers to a drug or chemical substance whose possession and use are controlled by law. The term "over-the-counter drug" refers to medicines and therapeutic agents that do not require a prescription. The term "disposal", as used herein, refers to the process of getting rid of a substance to a location at which the substance is rendered for no use.

The drug waste depository apparatuses disclosed herein include a housing having one or more waste input ports. In some cases, the waste input port/s may be configured to receive a variety of drug forms, but in other cases, the waste input port/s may be configured to receive a single form of a drug. For example, in some cases, the waste input port/s may be configured to only receive liquid drug waste via injection by a syringe. Regardless of the drug form/s the waste input port/s are configured to receive, the waste input port/s may, in some embodiments, be configured to make the retrieval of a drug deposited therein difficult and, in some embodiments, impossible. For instance, the waste input port/s may have an inlet channel which makes it difficult to route a suction tube therethrough, such as but not limited to a spiral, convoluted or tortuous channel. In addition or alternatively, the waste input port/s may have an inlet with a relatively small opening, particularly small enough such that an individual cannot place a hand through it. In any case, the apparatuses disclosed herein may be configured to prevent the housing from being opened other than by an authorized individual. For instance, the housing may be locked and/or may be tamper-proof. Furthermore, the apparatuses described herein may be configured for secure and tamper-proof attachment to a wall or flooring of a building such that the apparatuses cannot be removed from their location other than by an authorized individual.

In many cases, the drug waste depository apparatuses disclosed herein include a fluidics chamber disposed in the housing and configured to receive waste from the waste input port/s. In general, the fluidics chamber includes at least one fluid inlet to introduce fluid, such as but not limited to water, into the chamber to combine with the received waste and at least one fluid outlet for the removal of fluid therefrom. In some cases, the drug waste depository apparatuses disclosed herein may include a fluid supply container, either within the housing or external to the housing, from which fluid may be supplied to the fluidics chamber for processing of the waste therein. In some cases, the fluid supply container may be a refillable container accessible for an individual to refill prior to a waste cycle or as needed. Alternatively, the fluid supply container may be a replaceable pre-filled canister of fluid. In other cases, the drug waste depository apparatuses disclosed herein may be configured for attachment to a piped fluid line exterior to the apparatus. In any case, the fluid supplied to the fluidics chamber may, in some configurations, serve to dilute and/or dissolve the deposited waste for analysis and/or disposal. In addition or alternatively, the fluid supplied to the fluidics chamber may serve to wash the deposited waste from the fluidics chamber and/or from other chambers or fluid lines arranged in the housing downstream from the fluidics chamber. Any of such purposes may be applicable for applications in which an apparatus is configured to be used to collect drug waste in a form of liquids, pills, and powders.

In some configurations, the fluidics chamber may be fixedly arranged in the housing such that it is not readily removable from the housing. In yet other embodiments, the fluidics chamber may be readily removable from the housing. In such configurations, the fluidics chamber may be interchangeably referred to herein as a fluidics module since it may be swapped for other configurations of fluidics modules. In such cases, the drug waste depository apparatuses disclosed herein may be configured to accommodate and support a fluidics module, particularly having an interior space for receiving the fluidics module and arranged such that a fluid inlet and a fluid outlet of the fluidics module are respectively coupled to fluid supply and fluid waste lines in the housing.

Regardless of whether the fluidics chamber is fixedly arranged in the housing or is readily removable from the housing, the fluidics chamber may be arranged in the housing to receive drug waste directly from the waste input port/s. In other cases, the drug waste depository apparatuses disclosed herein may include one or more intermediary components between one or more of the waste input port/s and the fluidics chamber. For instance, the drug waste depository apparatuses disclosed herein may, in some embodiments, include an analytical device between one or more of the waste input port/s and the fluidics chamber, particularly if the apparatus is specifically used to collect liquid drug waste. In yet other embodiments, such as but not limited to cases in which a drug waste depository apparatus is specifically used to collect liquid drug waste, the apparatus may not include a fluidics chamber. In such cases, a drug waste depository apparatus may include a chamber disposed in the housing and configured to receive waste from the waste input port/s, but does not include a fluid inlet coupled to a fluid supply line. In such embodiments, the non-fluidic chamber may be fixedly arranged in the housing or may be readily removable from the housing.

In any case, the drug waste depository apparatuses disclosed herein may include a waste discharge line disposed within the housing and coupled to either a fluid outlet of a fluidics chamber or an outlet of another chamber in the housing. As set forth in more detail below, the waste discharge line may, in some cases, extend to a waste output port of the housing for collection or disposal of the waste exterior to the housing. In other embodiments, the waste discharge line may extend to a sequestration chamber disposed in the housing such that the waste may be stored until retrieved for testing, additional processing and/or disposal exterior to the housing. In yet other cases, the waste discharge line may extend to an adulteration chamber disposed in the housing such that the waste may be altered into a substance ready for disposal. In yet other embodiments, the drug waste depository apparatuses disclosed herein may be void of a waste discharge line. In such cases, the chamber coupled to the waste input port of the apparatus housing may serve as a sequestration or adulteration chamber of the apparatus and the apparatus may be configured such that the chamber as a whole (i.e., as a chamber module) or just the drug waste therein may be removed from the apparatus, such as but not limited to a door of the apparatus.

Further to the aforementioned components, the apparatuses disclosed herein include a processor and a storage medium with program instructions executable by the processor to affect operations of the apparatus. For example, the program instructions may be for controlling the supply of fluid to a fluidics chamber and/or controlling the discharge of fluid from the fluidics chamber. In some cases, the program instructions may be for supplying fluid to a fluidics chamber for each waste deposition in the apparatus. In such cases, the apparatus may include a sensor in the waste input port and/or the fluidics chamber for detecting the deposition of a material and, in response, the processor may send a command signal to route fluid to the fluidics chamber in accordance with the program instructions. In additional or alternative cases, the program instructions may be for supplying fluid to a fluidics chamber upon receiving information regarding a specific quantity, type, identification, or concentration of a drug. The information may be obtained from an electronic user input device on the apparatus or may be obtained via an analytical device in the apparatus. In any case, the amount of fluid supplied to the fluidics chamber may be the same each time or may, in some cases, be specific to information received regarding a specific volume, type, identification, or concentration of a drug. In addition or alternative to such program instructions affecting the amount and/or timing to control the supply or discharge of fluid, the apparatuses disclosed herein may include program instructions executable by the processor to affect other operations of the apparatus as explained in more detail below.

In general, the term "storage medium" as used herein, may refer to any electronic medium configured to hold one or more set of program instructions, such as but not limited to a read-only memory, a random-access memory, a magnetic or optical disk, or magnetic tape. The term "program instructions" may generally refer to commands within a program which are configured to perform a particular function, such as but not limited to receiving input, recording receipts of signals, sending output signals, and determining whether to allow an apparatus to start an operation. Program instructions may be implemented in any of various ways, including procedure-based techniques, component-based techniques, and/or object-oriented techniques, among others. Program instructions implementing the processes described herein may be transmitted over or on a carrier medium such as a wire, cable, or wireless transmission link.

As similarly described above for the fluidics chamber, the storage medium may, in some cases, be fixedly arranged in the housing such that it is not readily removable from the housing. In yet other embodiments, the storage medium may be readily removable from the housing such that it may be swapped with another storage medium having different or updated program instructions for affecting the operations of the drug waste depository apparatus. In such configurations, the storage medium may be referred to herein as a storage medium module since it may be swapped for other configurations of storage medium modules. In some cases, the storage medium and processor may be arranged in a common control/communications chamber. In some cases, the control/communications chamber may be fixedly arranged in the housing such that it is not readily removable from the housing. In yet other embodiments, the control/communications chamber may be readily removable from the housing such that it may be swapped with another control/communications chamber having different or updated processor and/or program instructions for affecting the operations of the drug waste depository apparatus. In such configurations, the control/communications chamber may be interchangeably referred to herein as a control/communications module since it may be swapped for other configurations of control/communications modules.

Depending on their intended use, the drug waste depository apparatuses disclosed herein may, in some cases, include an analytical chamber. In general, an analytical chamber considered for use in the drug waste depository apparatuses described herein is configured to determine or verify the identity, concentration and/or volume of a drug waste deposited therein. An analytical chamber may be either coupled directly to the waste input port of the housing of the drug waste depository apparatus or coupled indirectly to the waste input port via an intervening chamber in the apparatus, (i.e., the intervening chamber may be coupled between the waste input port and the analytical chamber and further an inlet of the analytical chamber may be coupled to an output of the intervening chamber). In the latter of such embodiments, an outlet of the analytical chamber may either be coupled directly to a waste discharge line of the drug waste depository apparatus or may be coupled to an inlet of the intervening chamber to cycle the drug waste back through the intervening chamber. In the former of such cases, the chamber may, in some embodiments, include another outlet coupled to the waste discharge line of the drug waste depository apparatus. Such a configuration may be particularly advantageous for embodiments in which the analytical chamber is selectively used or is in modular form and optionally placed in the drug waste depository apparatus. In any case, examples of an intervening chamber may be but is not limited to a fluidics chamber and/or a collection chamber.

Additional processing chambers which may be disposed in the housing of the drug waste depository apparatuses described herein include but are not limited to an adulteration chamber and/or a sequestration chamber. An adulteration chamber considered for use in the drug waste depository apparatuses described herein is configured to debase or make impure a drug waste by addition of other substance such that a usable form of the drug cannot be salvaged therefrom. A sequestration chamber considered for use in the drug waste depository apparatuses described herein is configured to store a drug waste and make it available to be retrieved from the apparatus. In general, an inlet of an adulteration chamber and/or an inlet of a sequestration chamber may be coupled (directly or indirectly via a waste discharge line) to a waste input port in the housing of the drug waste depository apparatus, one of the fluid outlets of a fluidics chamber, an outlet of an analytical chamber, or an outlet of an initial collection chamber in the apparatus.

In any case, the storage medium of a drug waste depository apparatus having an analytical chamber, an adulteration chamber and/or a sequestration chamber may generally include program instructions for controlling operations of such chambers and possibly selectively or randomly routing a drug waste to the chamber/s. In alternative embodiments, an apparatus may include program instructions for routing every drug waste deposited in the apparatus to the chamber/s (i.e., the routing of the drug waste to the chamber/s is neither selective nor random). Selective routing may be based on various parameters, including but not limited to identity information regarding one or more individuals depositing a drug in the waste input port (which as described in more detail below may be acquired by an electronic user interface of a drug waste depository apparatus and may include but is not limited to a name, occupation, employment department and/or personnel number of the user).

Other parameters constituting selective routing of a drug waste to an analytical chamber, an adulteration chamber and/or a sequestration chamber may be based on the time of day, day of the week, or date a drug waste is dispensed in the apparatus or upon information regarding a drug and/or an individual depositing a drug into the apparatus is received from an electronic user interface of the apparatus. In latter of such cases, the drug waste depository apparatus may include a real-time clock and program instructions for registering a time and date of the received information. In the former of such cases, the drug waste depository apparatus may include a sensor for detecting the receipt of drug waste within its waste input port or a chamber coupled thereto, a real-time clock, and program instructions for registering time and date upon receipt of a signal from the sensor indicating receipt of the drug waste. Yet other parameters constituting selective routing of a drug waste to an analytical chamber, an adulteration chamber and/or a sequestration chamber may be based on information of a drug entered into an electronic user interface (such as the quantity, type, identification, and/or concentration of a drug).

It is noted that knowledge by a user that a drug waste depository apparatus is configured to route a drug to an analytical chamber and/or a sequestration chamber in the apparatus (i.e., selectively, randomly, and/or for each waste cycle) may deter a person from trying to divert drug waste for illicit use. In particular, the knowledge that the drug waste may or will be analyzed for its content (i.e., identity, volume and/or concentration) and/or sequestered for further testing, additional processing and/or disposal exterior to the housing may deter a person from trying to divert drug waste for illicit use since the analytical and sequestration processes may lend to identifying the person of such activity. An advantage of a drug waste depository apparatus being configured to route a drug selectively or randomly to an analytical chamber and/or a sequestration chamber in the apparatus (versus routing drugs in such a manner for each waste cycle) is that an average processing time of waste cycles for the apparatus may be reduced, making the apparatus available to process more drug waste.

In any case, an analytical chamber, an adulteration chamber and/or a sequestration chamber may, in some embodiments, be fixedly arranged in the housing of a drug waste depository apparatus such that the chamber is not readily removable from the housing. In yet other cases, an analytical chamber, an adulteration chamber and/or a sequestration chamber may be readily removable from the housing of a drug waste depository apparatus. In such configurations, the analytical chamber, the adulteration chamber, the sequestration chamber may be interchangeably and respectively referred to herein as an analytical module, an adulteration module, a sequestration module since they may be swapped for other configurations of modules. A more detailed description of embodiments in which drug waste depository apparatuses include an analytical module, an adulteration module, and/or a sequestration module is provided below.

Other processing components which may be included in the drug waste depository apparatuses disclosed herein include but are not limited to an inlet water treatment chamber and a wastewater treatment chamber. In such cases, the storage medium of the drug waste depository apparatus may generally include program instructions for controlling operations of inlet water treatment chamber and/or the wastewater treatment chamber. In general, an inlet water treatment chamber considered for use in the drug waste depository apparatuses described herein is configured to treat and/or remove impurities in water prior to being supplied to the fluidics chamber. A wastewater treatment chamber considered for use in the drug waste depository apparatuses described herein is configured to prepare a waste stream for disposal, such as but not limited to testing the pH of the stream and adjusting it to be within a desired disposal range. In cases in which an apparatus includes a wastewater treatment chamber, the apparatus is configured such that for secure and tamper-proof attachment to a wastewater line of a building such that the effluent from the apparatuses cannot be tampered with for illicit purposes.

As described for the other processing components of the drug waste depository apparatuses disclosed herein, an inlet water treatment chamber and/or a wastewater treatment chamber may be fixedly arranged in the housing of a drug waste depository apparatus such that the chamber is not readily removable from the housing. In yet other embodiments, an inlet water treatment chamber and/or a wastewater treatment chamber may be readily removable from the housing of a drug waste depository apparatus. In such configurations, the inlet water treatment chamber and/or the wastewater treatment chamber may be interchangeably and respectively referred to herein as an inlet water treatment module and/or the wastewater treatment module since they may be swapped for other configurations of modules.

In addition to the chambers, modules, and program instructions discussed above, the drug waste depository apparatuses disclosed herein may include one or more other components, such as but not limited to a battery, a power cord and/or an electronic user interface. In general, an electronic user interface may be arranged along an exterior of the housing of a drug waste depository apparatus and have input controls to affect operation of apparatus, such as but not limited to a start and stop button to enable a user to start and terminate an operation of apparatus and/or input controls allowing selection of different operations conducted by the apparatus. In addition, an electronic user interface may include input controls for allowing entry of information by a user of the apparatus and, in some of such cases, the drug waste depository apparatus may include program instructions for conveying requests of such information on the electronic user interface (i.e., via an information conveying device as described below). Examples of information which may be requested and entered into an electronic user interface by a user may include but is not limited to user identification information (e.g., a name, occupation, employment department and/or personnel number of the user) and information regarding the drug waste being deposited in the drug waste depository apparatus (e.g., a name, code, quantity, and/or concentration of the drug).

Configurations of input controls on an electronic user interface may include any of those known in the art, including but not limited to buttons, switches, graphical user interfaces, touch sensor means, scanners, and means for enabling audible input. In some cases, an electronic user interface may include information conveying devices, such as visual indicators, visual displays, or audible means to inform a user of the apparatus about the status or operation of the drug waste depository apparatus. Examples of information regarding the status or operation of a drug waste depository apparatus which may be conveyed on an electronic user interface include but are not limited to the status of a door lock, indication if a waste cycle is in process or complete, the phase of the waste cycle (e.g., analytical, adulteration and/or sequestration), duration of the waste cycle or the time remaining, and/or errors in the operation of drug waste depository apparatus.

In some cases, the storage medium of the drug waste depository apparatuses disclosed herein may include program instructions executable by the processor to affect operations of the apparatus upon receipt of signals from the electronic user interface. For example, in some cases, a drug waste depository apparatus may prohibit entry of a drug waste into the waste input port of its housing or may prohibit entry of a drug waste into a chamber in the housing from the waste input port until information regarding an individual depositing a drug in the waste input port and/or information regarding quantity, type, identification, and/or concentration of the drug is entered into an electronic user interface of the apparatus. Other operations of a drug waste depository apparatus may be affected as well upon receipt of signals from an electronic user interface. For example, the information entered at the electronic user interface may be used to affect operation of a fluidics chamber, analytical chamber, a sequestration chamber and/or an adulteration chamber in the apparatus.

In some cases, the information entered at the electronic user interface may not be used to affect operation of a particular component in the apparatus, but yet may convey information to a user of the apparatus as if it were. In further cases, a drug waste depository apparatus may not include a particular processing chamber (such as a fluidics chamber, an analytical chamber, a sequestration chamber and/or an adulteration chamber), but yet the electronic user interface may convey information that a received drug waste is being or has been processed in a particular manner associated with such chambers. For example, in embodiments in which a drug waste deposit is not being analyzed in the apparatus (i.e., the drug waste depository apparatus is void of an analytical chamber or does not route the received drug to an analytic chamber in the apparatus), the electronic user interface may convey one or more requests for information regarding the user and/or the drug waste and, upon receiving such information, the electronic user interface may convey a message indicating the drug waste is being or has been analyzed. In addition or alternatively, the electronic user interface may convey such a message upon receipt of a signal that a drug waste has been received into the apparatus (such as via a sensor) even if the drug waste is not being analyzed by the depository apparatus. Similar tactics may also be utilized indicating a drug waste is being or has been sequestered for future testing, additional processing and/or disposal when in fact the apparatus does not route the drug waste to a sequestration chamber or does not include a sequestration chamber.

In any case, the thought that the drug waste will be analyzed for its content (i.e., identity, volume and/or concentration) and/or sequestered for further testing, additional processing and/or disposal exterior to the housing may deter a person from trying to divert drug waste for illicit use since the analytical and sequestration processes may lend to identifying the person of such activity. In some cases, upon receipt of user or drug information entered into an electronic user interface or upon receipt of signal that a drug waste has been received into the apparatus (such as via a sensor), the electronic user interface may convey a message indicating the drug waste is being or has been adulterated even if the drug waste depository apparatus does not route the drug waste to an adulteration chamber or is void of an adulteration chamber. Such a message may deter a person from trying to retrieve the drug waste from the drug waste depository apparatus for illicit purposes since the adulterated drug will likely have little or no physiological effect or may not be retrievable at all.

In yet other cases, a drug waste depository apparatus may be void of any indication regarding whether a deposited drug is to be analyzed, adulterated, or sequestered or even if the apparatus includes such modules in an effort to try to deter a person from trying to divert drug waste for illicit use. In particular as described in more detail below in reference to FIG. 1, a drug waste depository apparatus may be configured to receive a module for analyzing a drug, adulterating a drug, or sequestering a drug for further processing, but may be configured with opaque walls and an opaque door and further be void of any indicator of the processing of the drug therein or having modules do such processing. A lack of information regarding the contents and/or the processing of a drug by a drug waste depository apparatus, particularly by an apparatus known to have the capability to analyze, adulterate, and/or sequester a drug for further processing, may deter a person from trying to divert drug waste for illicit use since there is potential of being identified for such activity.

In some cases, the storage medium of the drug waste depository apparatuses described herein may include program instructions to create a record of information entered into the electronic user interface regarding a waste cycle and/or results from processing the drug waste through various components of the drug waste depository apparatus. In other embodiments, the storage medium may include program instructions to transmit such information to a separate device or system to create a record of such information. In either case, examples of information used to create a record of a waste cycle include but are not limited to user identification information, information regarding the drug waste being deposited in the drug waste depository apparatus, a serial number and physical location of the drug waste depository apparatus, data indicating whether or not the composition, concentration and/or quantity of the drug waste was verified or confirmed in an analytical chamber, and data indicating whether or not the drug waste was adulterated. In some embodiments, the storage medium of the drug waste depository apparatuses disclosed herein may include program instructions for creating a transaction code for a waste cycle and/or a time/date stamp indicating when the waste cycle was started and/or completed. Either or both of such information may be logged in a record of the waste cycle.

In some cases, the transaction code generated by the drug waste depository apparatuses disclosed herein may be reconciled with information regarding the dispensement of a drug from an automatic drug dispensing machine. Such a reconciliation process may be performed by any of the drug waste depository apparatuses disclosed herein, the automatic drug dispensing machine or a system separate from such apparatuses. In any case, the apparatus or system performing the reconciliation process includes a processor and a storage medium with program instructions which are executable by the processor for receiving a transaction code from a drug waste depository apparatus regarding collection of a drug and decoding the transaction code to determine identification information and parameter data of the drug. In addition, the apparatus or system performing the reconciliation process includes program instructions for reconciling the determined identification information and parameter data with identification information and parameter data generated by an automatic drug dispensing machine regarding the dispensement of the drug from the automatic drug dispensing machine.

As noted above, the drug waste depository apparatuses disclosed herein may, in some cases, include one or more processing modules that are readily removable from the housings of the apparatuses (i.e., as opposed to being fixedly arranged in the housings). In order to accommodate such versatility, the apparatuses disclosed herein may, in some cases, includes one or more interior spaces that are configured to receive and support one or more additional modules within the housing. For example, in some cases, the apparatuses described herein may include an interior space configured to receive an analytical module within the housing such that upon the analytical module occupying the interior space an inlet of the analytical module is coupled to either the waste input port of the apparatus or an outlet of a chamber in the apparatus. In addition or alternatively, the apparatuses described herein may include an interior space configured to receive a sequestration module and/or an adulteration module within the housing such that upon the sequestration module and/or the adulteration module occupying the interior space an inlet of the sequestration module and/or an inlet of the adulteration module is coupled to an outlet of a chamber in the apparatus, an outlet of an analytical chamber in the apparatus, or a waste discharge line of the apparatus.

It is contemplated that the drug waste depository apparatuses described herein may include an interior space configured to accommodate and support other types of modules in addition to or alternative to an analytical module, sequestration module and/or an adulteration module. For example, the apparatuses described herein may include an interior space configured to accommodate and support a fluidic chamber described above as a fluidics module. In addition or alternatively, the drug waste depository apparatuses described herein may include an interior space configured to accommodate and support a control/communications module comprising the processor and storage medium described above. Further yet, the drug waste depository apparatuses described herein may include an interior space configured to accommodate and support an inlet water treatment module or a wastewater treatment module. In other cases, any one or more of the chambers disclosed herein may not be removable from the housings of the apparatuses described herein.

In any case, a control/communications chamber/module of the drug waste depository apparatuses described herein may be configured to be in electrical communication with any processing chamber or processing module of the apparatus (i.e., upon a processing module occupying an interior space of the apparatus) and may include program instructions to affect their operations. The configurations to do so may include wired or wireless features. For instance, a control/communications chamber/module of the drug waste depository apparatuses described herein may, in some cases, include electrical connectors along its exterior surface for connection to a particular processing chamber/module such that when the processing module and/or the control/communications chamber/module is placed within designated space/s in the housing, the electrical connectors of the control/communications module mate with electrical connectors along an exterior of the processing chamber/module. In yet other embodiments, the control/communications module and processing chamber/module of the drug waste depository apparatuses described herein may include wireless transceivers for the transmission of information therebetween.

In any case, the inclusion of one or more interior spaces to accommodate and support one or more modules within the housings of the apparatuses described herein may generally allow the apparatuses to vary the functions it performs depending on the type of modules it includes. In addition, since the modules and interior spaces are encased within the housings of the apparatuses described herein, the housings are locked, and the housings are not transparent, users of the apparatuses described herein will not be aware of which modules may be contained in the apparatus at any given time. For example, a user will not know whether an apparatus includes an analytical module, sequestration module and/or the adulteration module and, thus, may be less inclined to try to divert drugs.

Furthermore, the inclusion of the one or more interior spaces may permit different configurations of the same type of module (e.g., different configurations of an analytical module, a sequestration module, an adulteration module, a fluidics module, and/or a control/communications module) to be used in the apparatuses described herein. In other words, having interior spaces in the housings of the apparatuses described herein may allow modules of the same type to be swappable, depending on the needs or desires of the facility in which the apparatus is arranged. Swapping modules may be beneficial for upgrading modules or changing modules for the disposal of different drugs. In some cases, it may be advantageous for the apparatuses described herein to allow for swappable control/communications modules, particularly with the swapping, addition, or removal of other modules in the housing such that a control/communications module used in the apparatus may be compatible with the modules it houses at any given time.

As set forth below, FIGS. 1 and 2 illustrate examples of drug waste depository systems and apparatuses having configurations to deter a person from trying to divert drug waste for illicit use. FIGS. 3 and 4 illustrate flowcharts of processes for operations of such drug waste depository apparatuses. FIGS. 5-7 illustrate examples of drug waste depository apparatuses including respectively different components and the flow drug waste and electrical connections among the components. Moreover, FIG. 8 depicts a flowchart of processes for reconciling information regarding a drug disposed of in an automatic controlled substance waste depository versus information regarding the dispensement of the drug from an automatic drug dispensing machine. It is noted the methods, apparatuses, and systems described herein are not limited to the depictions in the drawings. Several other arrangements of components and/or configurations of apparatuses may be considered. Furthermore, it is noted that the drawings are not necessarily drawn to scale.

Turning to FIG. 1, system 10 is shown including drug waste depository apparatus 12 and module 14. Drug waste depository apparatus 12 includes housing 16 with opaque walls 18 and opaque door 19 such that the contents in the interior of housing 16 is not visible when opaque door 19 is closed. Housing 16 further includes electronic user interface 17 and waste input port 15 for introducing a drug waste into the apparatus, particularly when opaque door 19 is closed. Waste input port 15 is shown on the upper surface of housing 16, but may alternatively be disposed along the side of opaque walls 18 depending on the design specifications of the apparatus. Regardless of the position of waste input port 15, drug waste depository apparatus 12 includes chamber 20 disposed in the housing to receive waste from waste input port 15, such as but not limited to being arranged in the upper portion of the interior of housing 16 in proximity to waste input port 15. In addition, drug waste depository apparatus 12 includes control/communications chamber 21 including a processor and a storage medium having program instructions executable by the process for affecting the operation of one or more components in drug waste depository apparatus 12 as discussed in more detail below. Alternatively, drug waste depository apparatus 12 need not include a chamber to house the processor and the storage medium.

Although not shown, chamber 20 has a waste inlet coupled to waste input port 15 and further has waste outlet 25. In some embodiments, chamber 20 may be a fluidics chamber and, in such cases, chamber 20 includes a fluid inlet in addition to the waste inlet coupled to waste input port 15. Furthermore, in such cases, drug waste depository apparatus 12 includes a fluid supply line coupled to the fluid inlet of chamber 20. In other cases, chamber 20 may not be a fluidics chamber and, thus, chamber 20 may not include a fluid inlet and drug waste depository apparatus 12 may not include a fluid line coupled to chamber 20. In any case, chamber 20 may, in some embodiments, include a recycle inlet for receiving a drug waste back from a module coupled to waste outlet 25. In addition or alternatively, chamber 20 may, in some embodiments, include an additional waste outlet (not shown) coupled to discharge line 22 in housing 16. Discharge line 22 may be coupled to another chamber in housing 16 or may be coupled to waste outlet 23 of housing 16 as shown in FIG. 1.

As further shown in FIG. 1, drug waste depository apparatus 12 includes interior space 26 within housing 16 separate from chamber 20 and accessible when opaque door 19 is open. In general, interior space 26 is configured to receive module 14 such that waste outlet 25 of chamber 20 may be coupled to inlet 24 of module 14. In addition, drug waste depository apparatus 12 is configured such that waste outlet 25 may be closed when interior space 26 is void of a module or, more specifically, when waste outlet 25 is not coupled to an inlet of another chamber. In general, module 14 is configured to sequester, analyze, and/or adulterate one or more drugs. In some cases, chamber 20 and module 14 may be configured such that the coupling of their respective waste outlet and inlet may be manually coupled by an individual placing module 14 into interior space 26. In some of such cases, waste outlet 25 of chamber 20 and inlet 24 of module 14 may be directly coupled together. In other embodiments, drug waste depository apparatus 12 may include a removable line to couple chamber 20 and module 14 together.

In yet other cases, drug waste depository apparatus 12 may be configured such that the coupling of waste outlet 25 of chamber 20 to inlet 24 of module 14 may be automatic when module 14 is properly inserted into interior 22. In some of such cases, the waste outlet of chamber 20 may be biased closed until it is engaged with inlet 24 of module 14. In particular, drug waste depository 12 may, in some embodiments, be configured to receive module 14 in close proximity to chamber 20 such that inlet 24 causes the waste outlet of chamber 20 to open when coming into alignment with waste outlet. In yet other cases, drug waste depository apparatus 12 may include sensor 28 for detecting presence of an item in interior space 26 and control/communications chamber 21 may include program instructions for opening the waste outlet of chamber 20 when sensor 28 detects the presence of an item in interior space 26 and program instructions for closing the waste outlet of chamber 20 when sensor 28 does not detect the presence of an item in interior space 26. In some embodiments, sensor 28 may be specific to detecting the presence of module 14 in interior space 26 and, more specifically, may be specific to detecting when module 14 has been properly inserted into interior space 26 such that inlet 24 of module 14 is in alignment with waste outlet 25 of chamber 20. In some cases, drug waste depository apparatus 12 may include an additional or alternative sensor for specifically detecting when waste outlet 25 is coupled to an inlet of another chamber.

In addition to the aforementioned components, drug waste depository apparatus 12 may include sensor 29 for detecting whether opaque door 19 is closed and/or open. In some embodiments, drug waste depository apparatus 12 may be void of an indicator of whether an item occupies or does not occupy interior space 26 when opaque door 19 is closed such as shown in FIG. 2 In particular, drug waste depository apparatus 12 being void of such an indicator as well as housing 16 having opaque walls 18 and opaque door 19 will not allow an individual dispensing a drug into drug waste port 15 to know how the drug will be processed, particularly if it will be analyzed, adulterated, and/or sequestered for further processing. Thus, such provisions may deter the individual from trying to divert the drug waste for illicit use.

In some cases, drug waste depository apparatus 12 may include one or more additional interior spaces within housing 16 which are configured for receiving one or more additional modules in system 10 that process or sequester a drug in a different manner than module 14. In yet other embodiments, drug waste depository apparatus 12 may include only include interior space 26 for receiving a single module selected from multiple different modules in system 10. In some of such cases, the multiple different modules may include a "dummy" module, which is only configured to pass the drug waste through the module to other chambers in housing 16 or to waste outlet 23 (i.e., it is not configured to analyze, sequester, or denature the drug waste). As a consequence, even if an individual dispensing a drug into drug waste port 15 is aware that the apparatus includes a module, the individual will not know which type of module is in the apparatus and whether or how the drug will be processed in the apparatus, deterring the individual from trying to divert the drug waste for illicit use. In any case, drug waste depository apparatus 12 may, in some embodiments, be one of multiple drug waste depository apparatuses in system 10 each configured in a similar manner as drug waste depository apparatus 12 for receiving one or more modules. Such a configuration of system 10 may be advantageous for a location or a building in which multiple drug waste depositories are needed and further for interchanging the modules among the apparatuses and/or periodically removing modules from some of the apparatuses to save time and money from processing the drug waste.

As noted above, FIGS. 3 and 4 illustrate flowcharts of processes for operations of drug waste depository apparatuses, such as but not limited to those depicted in FIGS. 1 and 2. The operation processes may generally be executed by program instructions of the drug waste depository apparatuses described herein. In particular, FIG. 3 illustrates a flowchart including block 30 in which user information and/or drug waste information is received and block 32 in which entry of drug waste into a chamber of a drug waste depository apparatus is allowed. In particular, a drug waste depository apparatus may, in some cases, prohibit entry of a drug waste into the waste input port of its housing or may prohibit entry of a drug waste into a chamber in the housing from the waste input port until information regarding an individual depositing a drug in the waste input port and/or information regarding quantity, type, identification, and/or concentration of the drug is entered into an electronic user interface of the apparatus. Furthermore, the flowchart depicted in FIG. 3 includes block 34 in which discharge of the drug waste from the chamber is controlled (i.e., opened or selectively opened) when an interior sensor detects presence of a supplemental module (i.e., a module in addition to the noted chamber).

FIG. 4 illustrates a flowchart including the same blocks 30 and 32 as FIG. 3, but instead of block 34, the flowchart includes block 36 in which drug waste is randomly or selectively routed from the noted chamber to another chamber in the drug waste depository apparatus. It is noted that the flowchart outlined in FIG. 4 is not specific to drug waste depository apparatuses which are able to accommodate removable modules for analyzing, sequestering, and/or adulterating one or more drugs, such as described above in reference to FIGS. 1-2 or below in reference to FIGS. 5-7. Rather, the flowchart of operation processes may also be applicable to drug waste depository apparatuses having fixed chambers for analyzing, sequestering, and/or adulterating one or more drugs, but includes provisions for controlling the discharge of drug waste to such chambers in a selective or random manner.

As set forth above, selective routing may be based on various parameters, including but not limited to identity information regarding one or more individuals depositing a drug in the waste input port (which as described in more detail below may be acquired by an electronic user interface of a drug waste depository apparatus and may include but is not limited to a name, occupation, employment department and/or personnel number of the user). Other parameters constituting selective routing of a drug waste to an analytical chamber, an adulteration chamber and/or a sequestration chamber may be based on the time of day, date, or day of the week a drug waste is dispensed in the apparatus or upon information regarding a drug and/or an individual depositing a drug into the apparatus is received from an electronic user interface of the apparatus. Yet other parameters constituting selective routing of a drug waste to an analytical chamber, an adulteration chamber and/or a sequestration chamber may be based on information of a drug entered into an electronic user interface (such as the quantity, type, identification, and/or concentration of a drug).

As noted above, FIGS. 5-7 illustrate schematic views of examples of drug waste depository apparatuses including respectively different components, with solid arrowed lines depicting drug waste flow and dotted arrowed lines depicting electrical connections between components. The apparatuses are specific to including fluidic chambers, but it is noted that such chambers may be replaced with non-fluidic chambers, depending on the design specifications of an apparatus. Turning to FIG. 5, drug waste depository apparatus is shown including housing 42 with waste input port 44 and fluidics chamber 45 disposed in the housing and configured to receive waste from waste input port 44. For the configuration of drug waste depository apparatus 40, fluidics chamber 45 includes fresh fluid inlet 46 coupled to deionized water container 48, waste discharge outlet 50 coupled to sequestration/adulteration module 52 as well as analytic fluid outlet 54 and analytic fluid inlet 56 respectively coupled to fluid inlet 60 and fluid outlet 62 of analytical module 58. In addition, drug waste depository apparatus 40 includes control/communications module 64 including a processor and program instructions executable by the processor for controlling operations of the apparatus, such as but not limited to the supply of fluid through at least fresh fluid inlet 46 of fluidics chamber 45 and/or controlling the discharge of fluid from at least waste discharge outlet 50 of fluidics chamber 45. As set forth above, drug waste depository apparatus 40 may include additional components than those shown in FIG. 1.

Turning to FIG. 6, drug waste depository apparatus 70 is shown having some of the same features as drug waste depository apparatus 40, particularly features with the same reference numbers as shown in FIG. 5. Descriptions of such features are not reiterated for the sake of brevity. As shown in FIG. 6, drug waste depository apparatus 70 is different from drug waste depository apparatus 40 in that drug waste depository apparatus 70 does not include sequestration/adulteration module 52, but instead includes a sequestration carousel 72 in sequestration module 74. Sequestration carousel 72 may generally include a device for storing multiple drug wastes (i.e., drug wastes from different waste cycles). In addition, drug waste depository apparatus 70 is different from drug waste depository apparatus 40 in that drug waste depository apparatus 70 does not include deionized water container 48, but instead includes inlet water treatment module 76. Furthermore, drug waste depository apparatus 40 is different from drug waste depository apparatus 40 in that drug waste depository apparatus 70 includes wastewater treatment module 48 as well as fluid inlet 80 and fluid outlet 82 along the exterior of housing 42.

Turning to FIG. 7, drug waste depository apparatus 90 is shown having some of the same features as drug waste depository apparatus 70, particularly features with the same reference numbers as shown in FIG. 6. Descriptions of such features are not reiterated for the sake of brevity. As shown in FIG. 7, drug waste depository apparatus 90 is different from drug waste depository apparatus 70 in that drug waste depository apparatus 90 does not include analytical module 58 leaving interior space 92 within housing 42 vacant. Interior space 92 is configured to receive and support an analytical module within housing 42 such that analytic fluid outlet 54 and analytic fluid inlet 56 of fluidic chamber 45 are respectively coupled to a fluid inlet and a fluid outlet of the analytical module upon the analytical module occupying the interior space.

As further shown in FIG. 7, drug waste depository apparatus 90 is different from drug waste depository apparatus 70 in that drug waste depository apparatus 90 includes removable fluid line 94 coupled between analytic fluid outlet 54 and the analytic fluid inlet 56, wherein interior space 92 in the housing is configured to receive an analytical module such that analytic fluid outlet 54 and analytic fluid inlet 56 are respectively coupled to a fluid inlet and a fluid outlet of the analytical module upon removable fluid line 94 being decoupled from analytic fluid outlet 54 and analytic fluid inlet 56 and upon the analytical module occupying interior space 92. In alternative configurations, removable fluid line 94 may be omitted from drug waste depository apparatus 90. In some of such cases, analytic fluid outlet 54 and analytic fluid inlet 56 may be biased closed until the analytic fluid outlet and the analytic fluid inlet are respectively coupled to the fluid inlet and the fluid outlet of an incoming analytical module. In yet other cases, control/communications module 64 may include program instructions for opening and closing of analytic fluid inlet 54 and analytic fluid outlet 56 of fluidics chamber 45 subsequent to an analytical module occupying interior space 92. In any of such cases, drug waste depository apparatus 90 is configured such that the processor of control/communications module 64 is in electrical communication with an analytical module upon the analytical module occupying interior space 92. In addition, control/communications module 64 includes program instructions to affect operations of an analytical module occupying interior space 92.

It is noted that configurations similar to those described above to ensure proper fluid connection between a fluidics chamber and an incoming analytical module of a drug waste depository apparatus may be used to insure proper fluid connection between a fluidics chamber and other incoming modules of a drug waste depository apparatus, such as but not limited to a sequestration module and/or an adulteration module. For example, the drug waste depository apparatuses described herein may include a removable fluid line coupled between a waste discharge line and either a fluid output of a fluidics chamber or a fluid output of an analytical chamber. In such cases, an interior space of the drug waste depository apparatuses may be configured such that upon the removable fluid line being removed from the fluid outlet of the fluidics chamber or from the fluid outlet of the analytical chamber and upon a sequestration module and/or an adulteration module occupying the interior space, the fluid outlet of the fluidics chamber or the fluid outlet of the analytical chamber is coupled to the fluid inlet of the sequestration module and/or the fluid inlet of the adulteration module. In some other cases, the fluidics chamber or analytical chamber of a drug waste depository apparatus may include an additional fluid outlet which is biased closed until the additional fluid outlet is respectively coupled to a fluid inlet of an incoming sequestration module or of an incoming adulteration module. In yet other cases, control/communications module 34 may include program instructions for selectively opening fluid outlets of a fluidics chamber or analytical chamber of drug waste depository apparatus such that fluid can be routed from such chambers to a processing module when the module is inserted into the apparatus.

Further to the aforementioned ideas of drug waste depository apparatuses having one or more interior spaces to accommodate and support removable modules as well as other configurations to make it impossible for a person depositing waste in the apparatus to know whether the apparatus includes an analytical chamber, a sequestration chamber and/or an adulteration chamber, it is contemplated that different drug waste depository apparatuses having different interior components and capabilities may be crafted to have the same exterior housing (such as but not limited to having same size, shape, electronic user interface and input controls) to make it impossible for a person depositing waste in the apparatus to know the capabilities of apparatuses. In such cases, the different drug waste depository apparatuses may be swappable with each other, depending on the needs of the facility in which they are used. Each of the swappable drug waste depository apparatuses may be configured for secure and tamper-proof attachment to a wall or flooring of a building as well as to wastewater lines of the building such that the apparatuses cannot be removed and swapped from their location other than by an authorized individual.

As noted above, FIG. 8 is a flowchart of processes for reconciling information regarding a drug disposed of in an automatic controlled substance waste depository versus information regarding the dispensement of the drug from an automatic drug dispensing machine. The processes may generally be executed via program instructions and a processor. It is noted that the flowchart outlined in FIG. 8 is not specific to drug waste depository apparatuses which are able to accommodate removable modules for analyzing, sequestering, and/or adulterating one or more drugs, such as described above in reference to FIGS. 1-2 and 5-7. Rather, the flowchart of operation processes may be applicable to any drug waste depository apparatus. As shown in FIG. 8, the flowchart includes block 96 in which a transaction code is received from an automated controlled substance waste depository device regarding collection of a controlled substance and block 97 for decoding the transaction code to determine identification information and parameter data of the controlled substance. In addition, the flowchart in FIG. 8 includes block 98 in which the determined identification information and parameter data is reconciled with identification information and parameter data generated by an automatic drug dispensing machine regarding the dispensement of the controlled substance from the automatic drug dispensing machine.

It will be appreciated to those skilled in the art having the benefit of this disclosure that this invention is believed to provide apparatuses, systems, and methods for collecting and disposing of drugs. Further modifications and alternative embodiments of various aspects of the invention will be apparent to those skilled in the art in view of this description. For example, although the disclosure provided herein focuses on the collection and disposal of drugs, the methods, apparatuses, and systems may be used for collection and disposal of substances other than drugs. Examples of substances which may have particular application include but are not limited to non-drug controlled substances, such as controlled chemicals or materials including controlled chemicals. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. The term "approximately" as used herein refers to variations of up to +/−5% of the stated number.

What is claimed:

1. A drug waste depository apparatus, comprising:

a housing having opaque walls, an opaque door, and a waste input port;

a chamber disposed within the housing, wherein the chamber comprises a waste inlet coupled to the waste input port;

an interior space within the housing separate from the chamber and accessible when the opaque door is open;

a first sensor for detecting presence of an item in the interior space; and a second sensor for detecting whether the opaque door is closed, wherein the apparatus is void of an indicator of whether an item occupies or does not occupy the interior space when the opaque door is closed.

2. The drug waste depository apparatus of claim 1, further comprising a removable module disposed within the interior space, wherein the removable module is configured to sequester, analyze, and/or adulterate one or more drugs, and wherein the removable module comprises an inlet coupled to a waste outlet of the chamber.

3. The drug waste depository apparatus of claim 2, wherein the drug waste depository apparatus further comprises a processor and a storage medium comprising program instructions executable by the processor for randomly and/or selectively allowing discharge from the waste outlet of the chamber to the removable module.

4. The drug waste depository apparatus of claim 2, wherein the chamber comprises a recycle inlet distinct from the waste inlet, and wherein the removable module comprises an outlet coupled to the recycle inlet.

5. The drug waste depository apparatus of claim 1, wherein the opaque door is lockable and tamper-proof.

6. The drug waste depository apparatus of claim 1, wherein the chamber is a fluidics chamber comprising a fluid inlet distinct from the waste inlet, and wherein the drug waste depository apparatus further comprises a fluid supply line coupled to the fluid inlet.

7. The drug waste depository apparatus of claim 1, further comprising an electronic user interface having input controls to affect operation of the apparatus.

8. A system, comprising:

one or more modules each configured to sequester, analyze, and/or adulterate one or more drugs; and one or more drug waste depository apparatuses each comprising:

a housing having a waste input port;

a chamber disposed in the housing, wherein the chamber comprises:

a waste inlet coupled to the waste input port; and a waste outlet;

an interior space in the housing configured to receive one of the one or more modules, wherein the system is configured such that the waste outlet of the chamber may be coupled to an inlet of a received module, and wherein the system is configured for the waste outlet of the chamber to be closable when the interior space is void of a module;

an electronic user interface;

a first sensor for detecting the presence of one of the one or more modules in the interior space;

a processor; and a storage medium comprising program instructions executable by the processor for:

receiving information from the electronic user interface regarding:

an individual depositing a drug in the waste input port; and/or quantity, type, identification, and/or concentration of a drug;

inhibiting waste disposal into the waste input port of the housing or restricting discharge from the waste input port of the housing to the waste inlet of the chamber prior to receiving the information from the electronic user interface; and subsequent to receipt of the information and regardless of whether the first sensor detects presence of a received module in the interior space, allowing discharge of drug waste into the waste input port of the housing and/or allowing discharge from the waste input port of the housing to the waste inlet of the chamber.

9. The system of claim 8, wherein the program instructions are further executable by the processor for controlling discharge from the waste outlet of the chamber to the inlet of a received module when the first sensor detects presence of one of the one or more modules in the interior space.

10. The system of claim 8, wherein the waste outlet of the chamber is biased closed until one of the one or more modules is inserted into the interior space and such that an inlet of the received module is aligned the waste outlet of the chamber.

11. The system of claim 8, wherein the chamber comprises an additional inlet distinct from the waste inlet, wherein the system further comprises a removable line configured to be coupled and decoupled between additional inlet and the waste outlet.

12. The system of claim 8, wherein the program instructions are further executable by the processor to affect operations of any one of the one or more modules when occupying the interior space.

13. The system of claim 8, wherein the chamber of at least some of the one or more drug waste depository apparatuses is a fluidics chamber comprising a fluid inlet distinct from the waste inlet of the chamber, and wherein the respective one or more drug waste depository apparatuses further comprise a fluid supply line coupled to the fluid inlet.

14. The system of claim 8, wherein at least one of the one or more drug waste depository apparatuses comprises one or more additional interior spaces in its housing, wherein the one or more additional interior spaces are respectively configured to receive a different module of the one or more modules.

15. A drug waste depository apparatus, comprising:

a housing having a waste input port;

a first chamber disposed in the housing, wherein the first chamber comprises:

a waste inlet coupled to the waste input port; and a waste outlet;

a second chamber disposed within the housing and having an inlet coupled to the waste outlet of the first chamber;

an electronic user interface;

a real-time clock;

a processor; and a storage medium comprising program instructions executable by the processor for:

receiving information from the electronic user interface regarding an individual depositing a drug in the waste input port;

registering a time and date of the received information; and randomly routing fluid from the first chamber to the second chamber or selectively routing fluid from the first chamber to the second chamber based on the time of day, date, or day of the week registered for the received information.

16. The drug waste depository apparatus of claim 15, wherein the received information is a name, occupation, employment department, and/or personnel number of the individual.

17. The drug waste depository apparatus of claim 15, wherein the chamber is a fluidics chamber comprising a fluid inlet distinct from the waste inlet of the chamber, and wherein the drug waste depository apparatus further comprises a fluid supply line coupled to the fluid inlet.

18. A system, comprising:

one or more modules each configured to sequester, analyze, and/or adulterate one or more drugs;

one or more drug waste depository apparatuses each comprising:

a housing having a waste input port;

a chamber disposed in the housing, wherein the chamber comprises:

a waste inlet coupled to the waste input port; and a waste outlet; and an interior space in the housing configured to receive one of the one or more modules, wherein the system is configured such that the waste outlet of the chamber may be coupled to an inlet of a received module, and wherein the waste outlet of the chamber is biased closed until it is coupled with an inlet of a received module;

a sensor for detecting when an inlet of a received module is coupled to the waste outlet of the chamber;

a processor; and a storage medium comprising program instructions executable by the processor for opening the waste outlet of the chamber upon receiving a signal from the sensor indicating an inlet of a received module is coupled to the waste outlet.

19. A system, comprising:

one or more modules each configured to sequester, analyze, and/or adulterate one or more drugs;

one or more drug waste depository apparatuses each comprising:

a housing having a waste input port;

a chamber disposed in the housing, wherein the chamber comprises:

a waste inlet coupled to the waste input port; and a waste outlet; and an interior space in the housing configured to receive one of the one or more modules, wherein the system is configured such that the waste outlet of the chamber may be coupled to an inlet of a received module, wherein the waste outlet of the chamber is biased closed until it is coupled with an inlet of a received module, and wherein the one or more modules are configured to open the waste outlet of the chamber upon coupling its inlet to the waste outlet.

\* \* \* \* \*